United States Patent [19]

Basford et al.

[11] 4,409,529
[45] Oct. 11, 1983

[54] PROSTHESIS

[75] Inventors: Robert Basford, Fetcham; David Hart, Keighley; David Hawkins, Bifleet; David Knight, Worcester Park; Roger Sidey, Richmond, all of England

[73] Assignee: Hugh Steeper Limited, London, England

[21] Appl. No.: 247,117

[22] Filed: Mar. 24, 1981

[30] Foreign Application Priority Data

Mar. 24, 1980 [GB] United Kingdom ............... 8009850
Sep. 23, 1980 [GB] United Kingdom ............... 8030680

[51] Int. Cl.³ .............................................. G05B 1/06
[52] U.S. Cl. ................................. 318/653; 318/568; 318/662; 318/647; 318/376; 3/1.1
[58] Field of Search .................. 3/1.1; 318/653, 647, 318/662, 568, 376

[56] References Cited

U.S. PATENT DOCUMENTS

| | | | |
|---|---|---|---|
| 3,557,387 | 1/1971 | Ohlenbusch | 3./1.1 |
| 3,609,769 | 10/1971 | Suzuki et al. | 3/1.1. |
| 3,683,423 | 8/1972 | Cradanzano | 3/1.1 |
| 3,866,246 | 2/1975 | Seamone et al. | 3/1.1 |
| 3,883,900 | 5/1975 | Jerard | 3/1.1 |
| 3,888,201 | 6/1975 | Zuvela | 318/647 X |
| 4,246,661 | 1/1981 | Pinson | 3/1.1 |
| 4,319,170 | 3/1982 | Brent | 318/258 |

Primary Examiner—B. Dobeck
Attorney, Agent, or Firm—Berman, Aisenberg & Platt

[57] ABSTRACT

A prosthesis comprising:
(a) a gripping member;
(b) an operating lever mounted to pivot about a pivot axis and operatively connected to the gripping member;
(c) a power unit including an electric motor, and a drive shaft rotatable by said electric motor;
(d) means connecting the drive shaft to the operating lever at a region spaced from the said pivot axis of the operating lever, said connecting means being constructed so that when the drive shaft rotates the connecting means (and also the region of the operating lever connected to the shaft) travels axially along the shaft thereby causing the operating lever to pivot about its pivot axis; and
(e) means pivotally mounting said power unit to allow the connecting means to move along an arcuate path about the pivot axis during pivoting of the operating lever.

23 Claims, 16 Drawing Figures

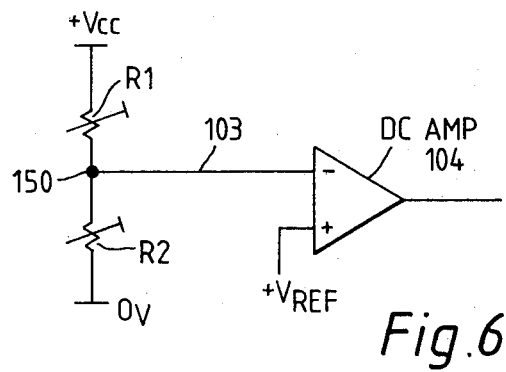
Fig.6
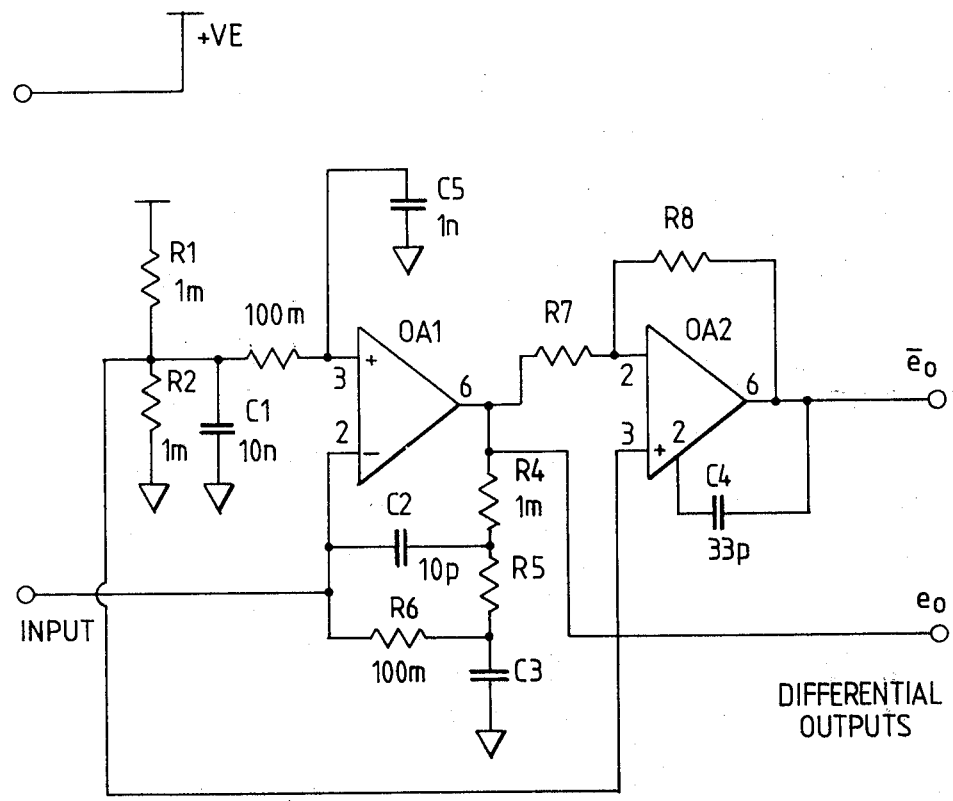
Fig 7.2

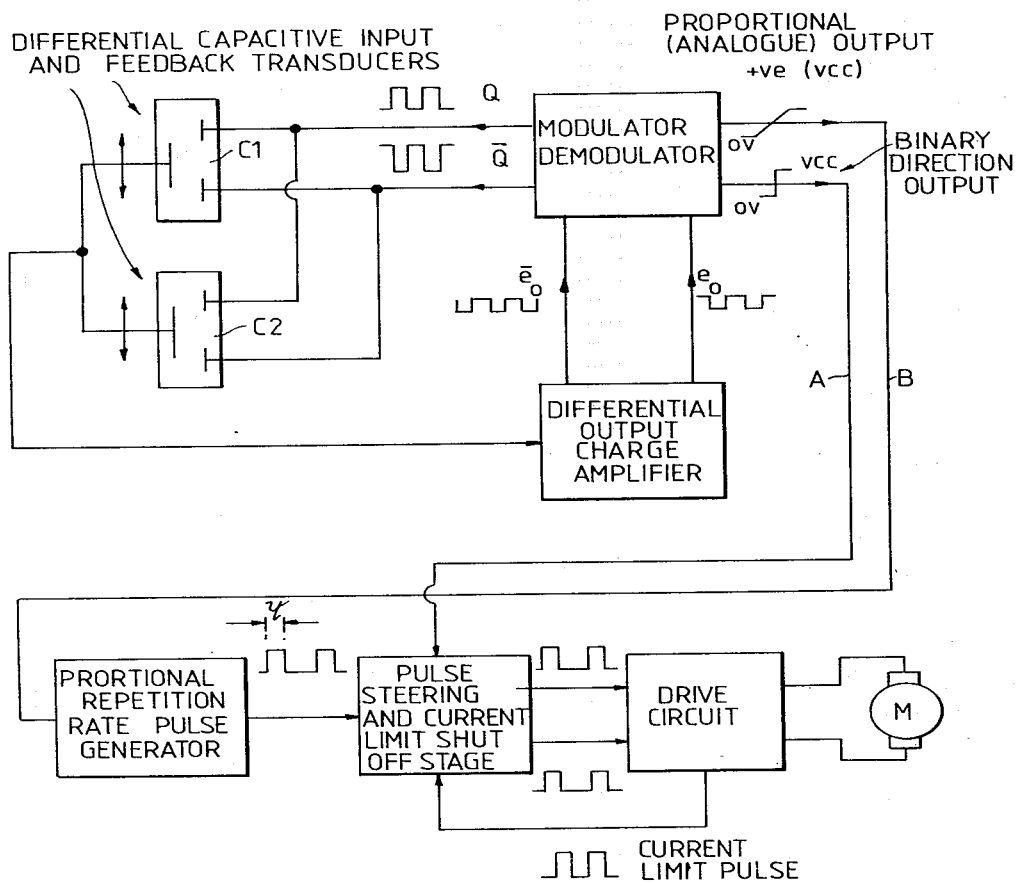
*Fig 7.1*

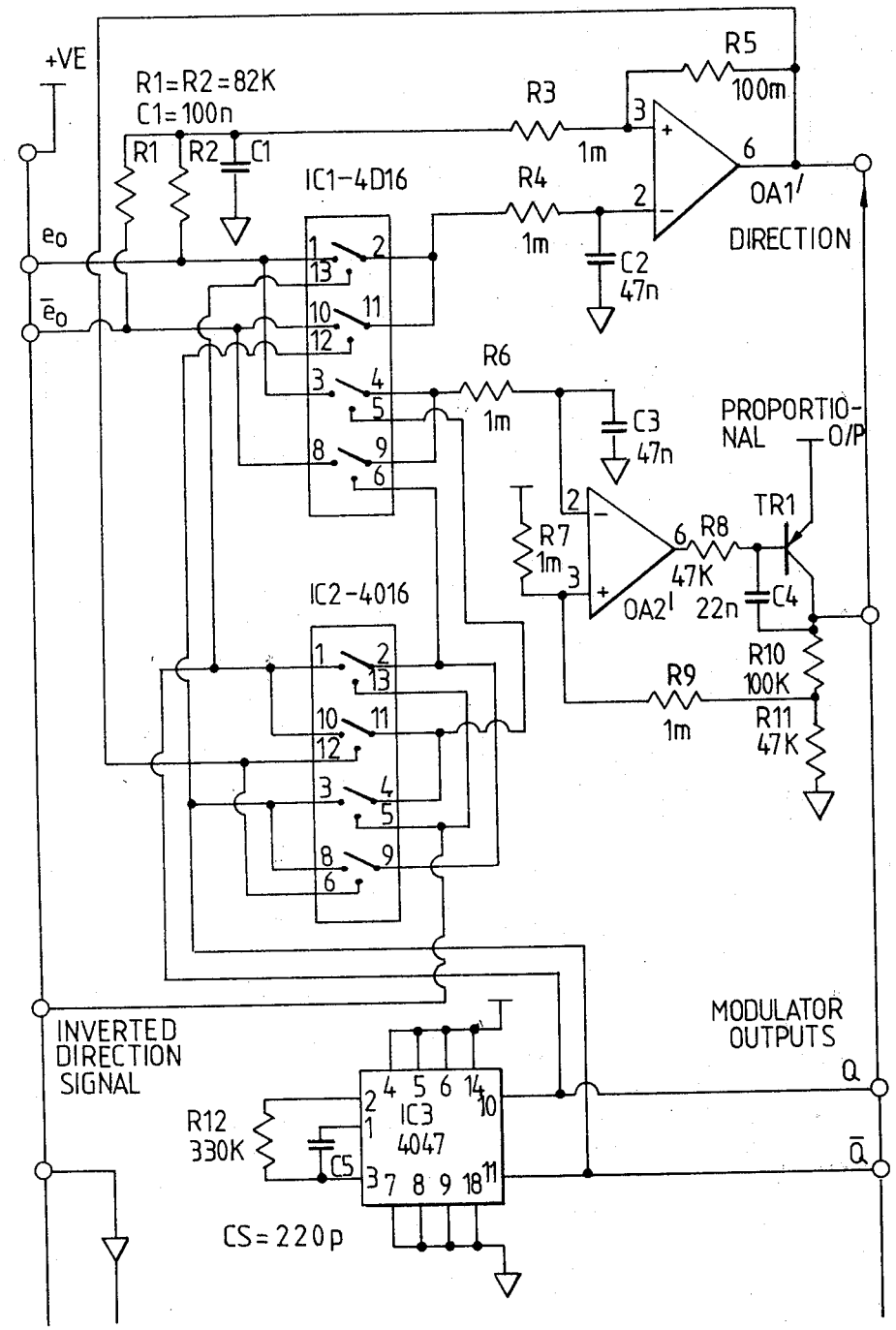
Fig 7.3

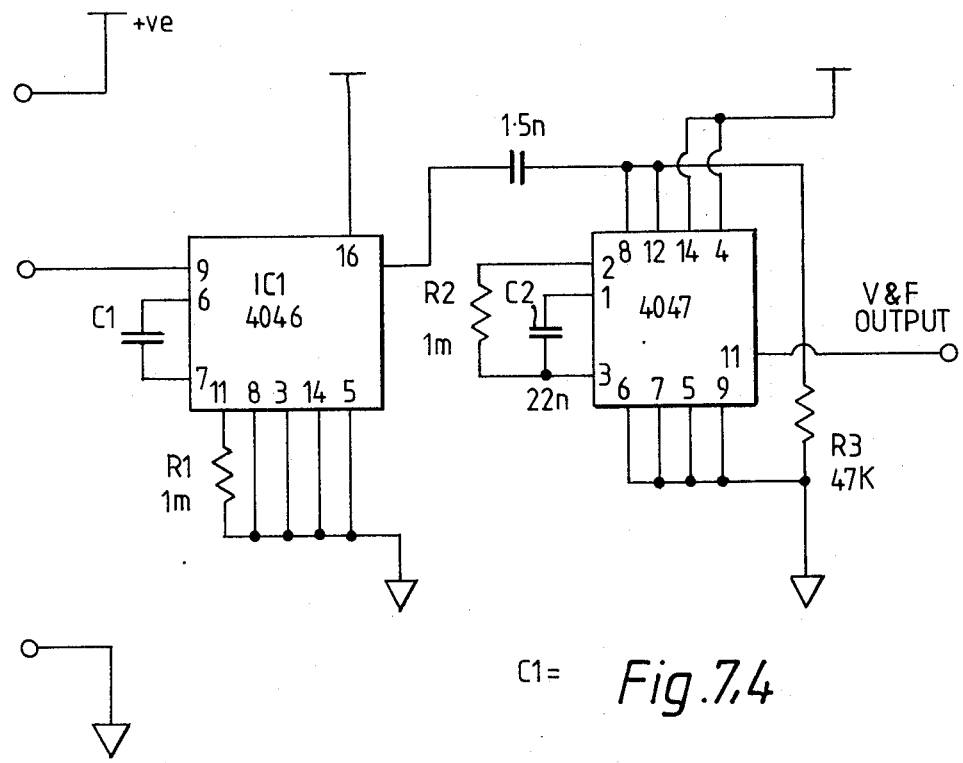
Fig. 7.4
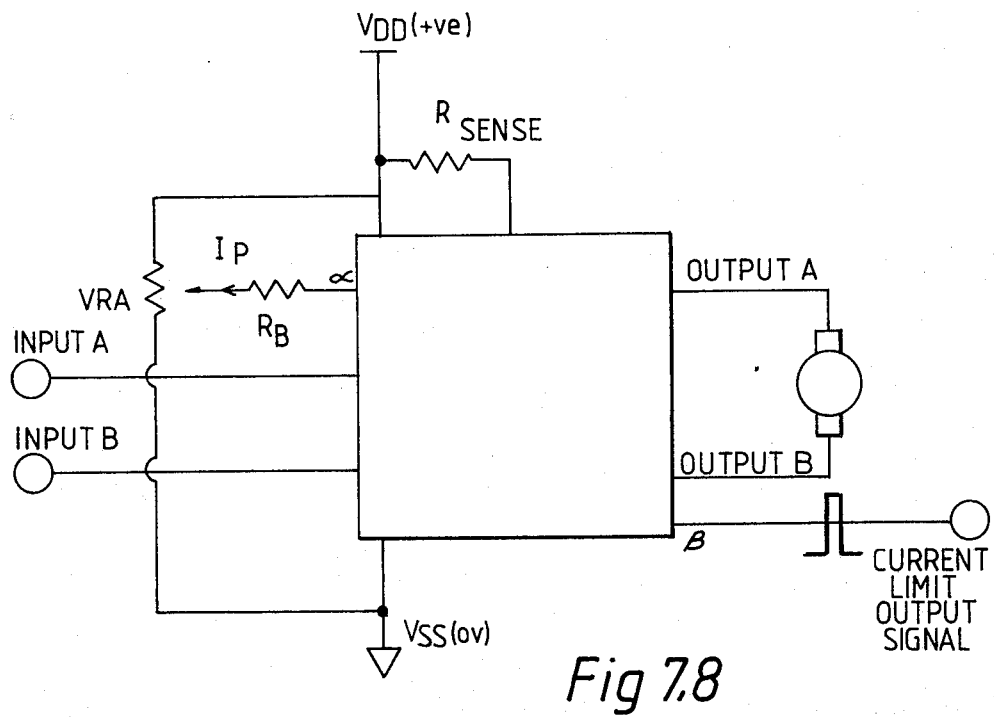
Fig 7.8

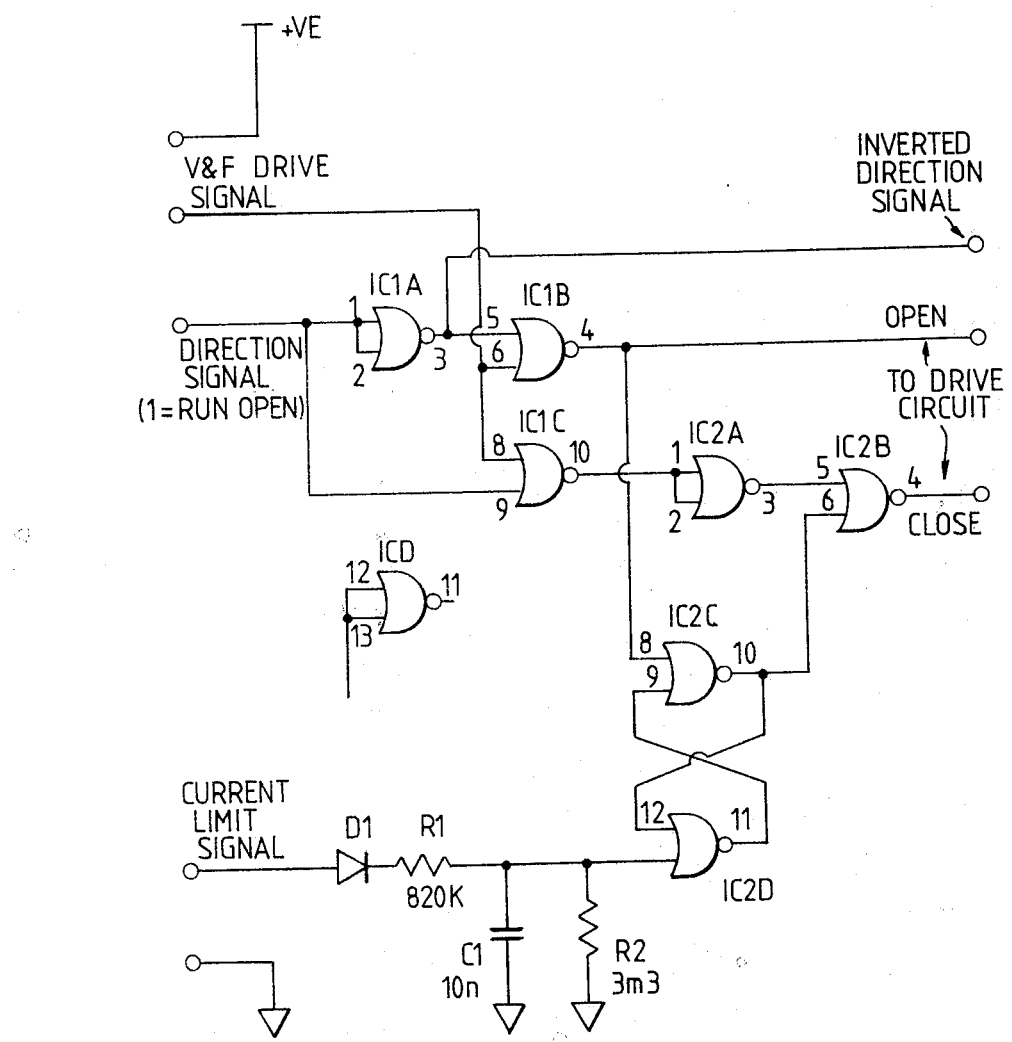
Fig 7.5    IC1,IC2 = 4001

MISSING PAGE TEMPORARY NOTICE

PATENT # 4409529 FOR ISSUE DATE 10-11-83

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

DRAWING SHEET # 11

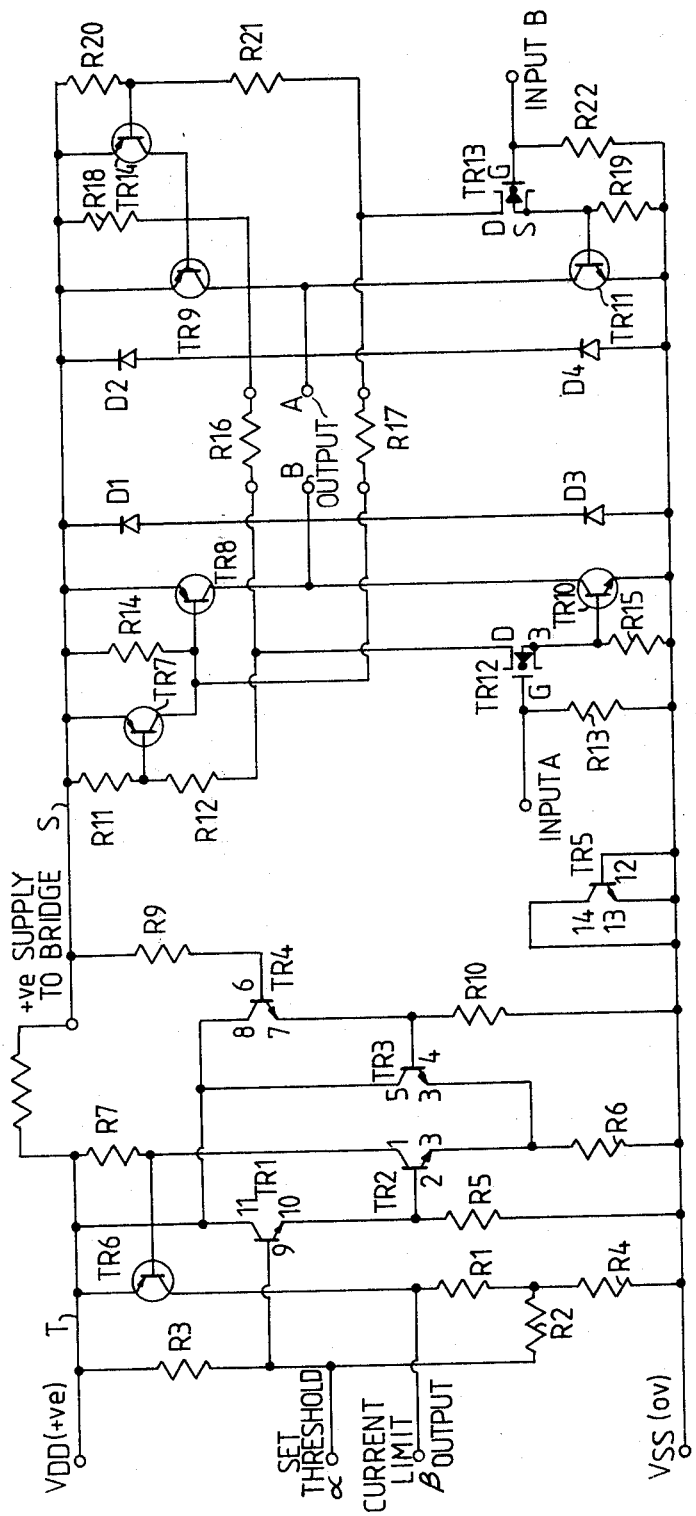
Fig. 7.7.

PROSTHESIS

This invention relates to a prosthesis, such as a mechanical hand, operated by an electric motor. The invention also relates to a control system which can be used to control the operation of the electric motor of a power operated mechanical hand, but which can also be used to control the operation of other motors and of electro-mechanical devices in general.

According to the present invention there is provided a prosthetic, for example a mechanical hand, in which a gripping member is arranged to be pivoted by pivoting an operating lever, the operating lever being connected at a region spaced from its pivot mounting to the output shaft of an electric motor by a connection (e.g. a screw-thread connection) so designed that rotation of the shaft causes the lever end region to move axially along the shaft to pivot the lever, the motor itself being pivotally mounted to allow the connection between the shaft and the operating lever to move through an arcuate path about the pivot mounting as the operating lever pivots.

The output shaft can be screw threaded, and the connection can comprise a nut threaded on the shaft.

The operating lever is preferably integral with or directly connected to the gripping member, although it would be possible for the lever to operate the gripping member by way of gearing or a linkage. Whichever arrangement is used, it is preferable for the operating lever to be connected with an operating lever of a second gripping member whereby the gripping members may be operated simultaneously to co-operate in gripping an article. This can be achieved by providing a pin on the nut or on the operating lever of the first gripping member, the pin being engaged in a slot in the operating lever of the second gripping member.

According to another aspect of the invention, there is provided a servo control system in which a motor is used to move a movable member, the system having first and second variable transducers comprises by two induction, two resistors, or two capacitors, the first transducer being personally variable to effect energisation of the motor to move the movable member, the value at which the first variable transducer is set determining a desired position to which the movable member is to be moved, the second transducer being drivingly connected with the movable member so that the second inductor is varied as the movable member moves, the two transducers being part of a closed-loop control circuit which, in response to a change of value of the personally-variable transducer, drives the motor a sense to vary the value of the second transducer in a sense to tend to restore the sum of the values of the transducers to a predetermined value.

According to a further aspect of the invention there is provided apparatus, for example a prosthesis, incorporating a member movable by an electric motor (as defined herein), operation of the electric motor being controlled by a control circuit, the circuit in one state thereof conditioning the motor to drive the member in one sense, in another state conditioning the motor to drive the member in the opposite sense, and in yet another state thereof conditioning the motor to act as a brake to retard motion of said member.

The term "motor" in this context means any device for producing motion, whether rotational or linear.

Preferably the motor is a direct current electric motor caused to drive said member in one sense by passing electrical current through it in one direction, caused to drive said member in the opposite sense by passing electrical current through it in a second and opposite direction, and caused to operate as a brake by providing a high conductivity shunt across the motor. The electric motor may be rotary, linear, a simple solenoid, or other electromechanical device.

According to another aspect of the invention, there is provided a servo control system in which a motor is used to move a member, the system having one or both of the following two features:

(a) the inductance of an inductor is variable to effect energisation of the motor to move the movable member;
(b) the inductance of an inductor is arranged to vary as the movable member moves whereby to provide a feedback signal indicative of the position of the movable member.

In one embodiment both inductors are provided, one inductor being personally variable to select a desired position of the movable member, and the other inductor being arranged to be varied as the member moves. In this particular case, a closed-loop control circuit may be provided which, in response to a change of inductance of the personally-variable inductor, drives the motor in sense to vary the inductance of the feedback inductor so as to tend to restore the sum of the inductances to a predetermined value.

It is preferred to arrange the control circuit so that a change of the inductance of the personally-variable inductor frequency modulates an oscillator circuit. In this case, the modulated output of the oscillator is demodulated, and the demodulated signal is used to drive the motor. The demodulated signal can be used to provide a series of pulses for driving the motor, and it is preferred to arrange the circuit so that the duty cycle depends on the amount by which the total inductance of the two inductors deviates from the predetermined value.

In order to determine the direction in which the motor is driven to move the member, a comparator may be used to compate the demodulated signal with a reference voltage and to gate the motor drive signals according to whether the demodulated signal is at a higher lever or lower level than the reference voltage. It is preferred to amplify the demodulated signal before feeding it to the comparator.

In a modified embodiment which is a mechanical equivalent of the two-inductor system, a single inductor can be used, the inductance of the inductor being variable both personally (e.g. by moving an inductor core) and also automatically as the movable member moves (e.g. by moving an inductor coil).

In an alternative embodiment also operable in closed loop mode, the personally operable inductor can be replaced by any other suitable device, e.g. a device producing a voltage control signal fed to the d.c. amplifier, to be compared with the reference voltage. This voltage control signal could be derived from muscle movement or from electromyograph signals.

It is also possible to dispense with the feedback inductor to give operation in open loop mode.

The inductor or inductors can conveniently comprise cores movable in coils. This arrangement can be designed to give a small low friction inductor, and the cores can be moved by pull cords against the bias of a restoring spring. Alternatively, the personally operable inductor could be varied by a rotatable control knob.

Preferred embodiments of the invention will now be described by way of example and with reference to the accompanying drawings in which:

FIG. 6 is a detail showing a modification of the circuit of FIG. 5;

FIG. 7.1 is a schematic block diagram showing another control circuit operative in closed loop mode, which circuit can be used to control the operation of the motor of the mechanical hand;

FIG. 7.2 is a circuit diagram of a charge amplifier of the circuit of FIG. 7.1;

FIG. 7.3 is a diagram of a modulator-demodulator of the circuit of FIG. 7.1;

FIG. 7.4 is a diagram of a voltage to frequency converter and monostable unit of the circuit of FIG. 7.1;

FIG. 7.5 is a diagram of a current limit latch and pulse steering unit of the circuit of FIG. 7.1;

FIG. 7.6 is a diagram showing an alternative circuit to the circuit of FIG. 7.5;

FIG. 7.7 is a diagram of a motor driving stage of the circuit of FIG. 7.1; and

Figure 5:
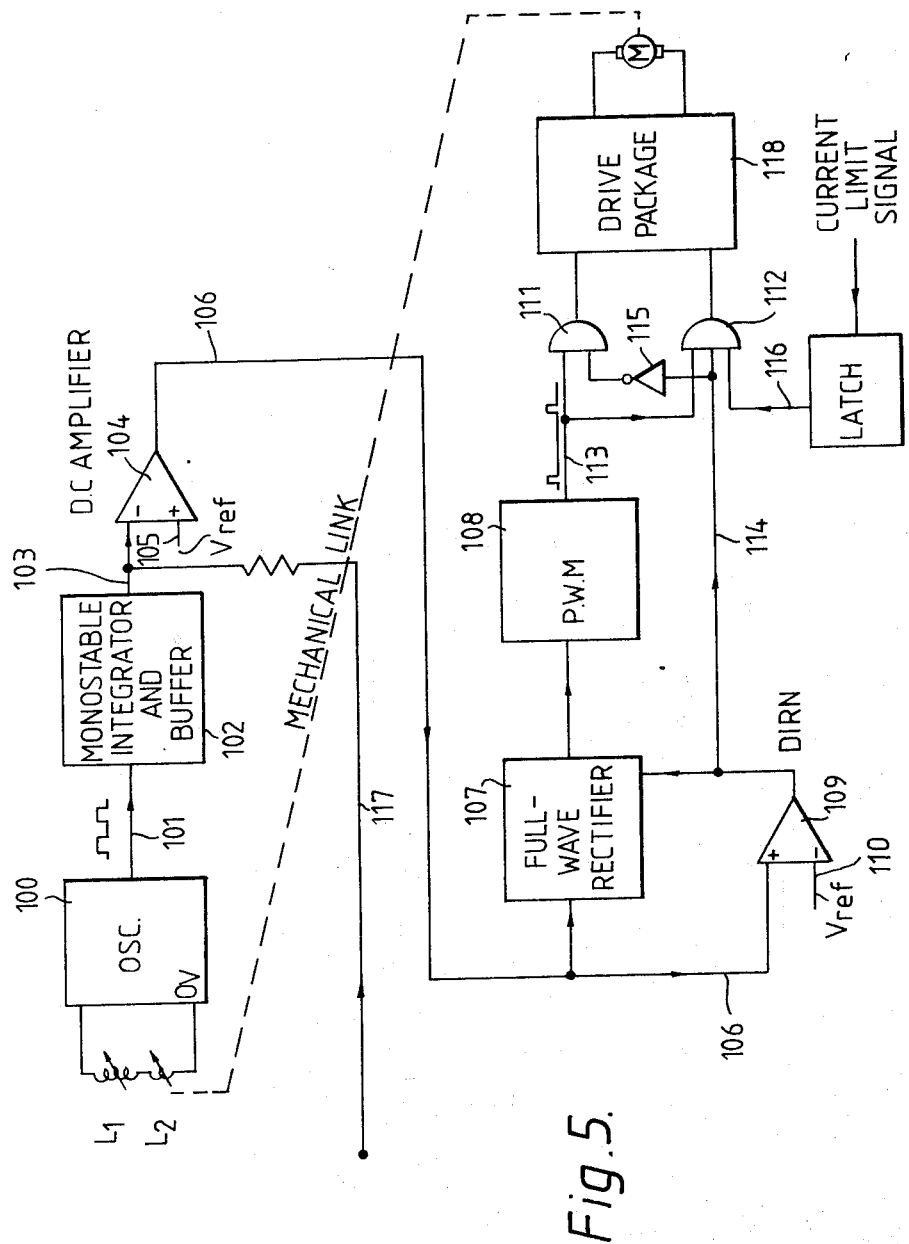
FIG. 5 is a circuit diagram showing one circuit which could be used to operate the prosthesis of FIGS. 1-4.

FIG. 7.8 is a diagram showing how the circuit of FIG. 5.7 will be connected up in use.

Figure 1:
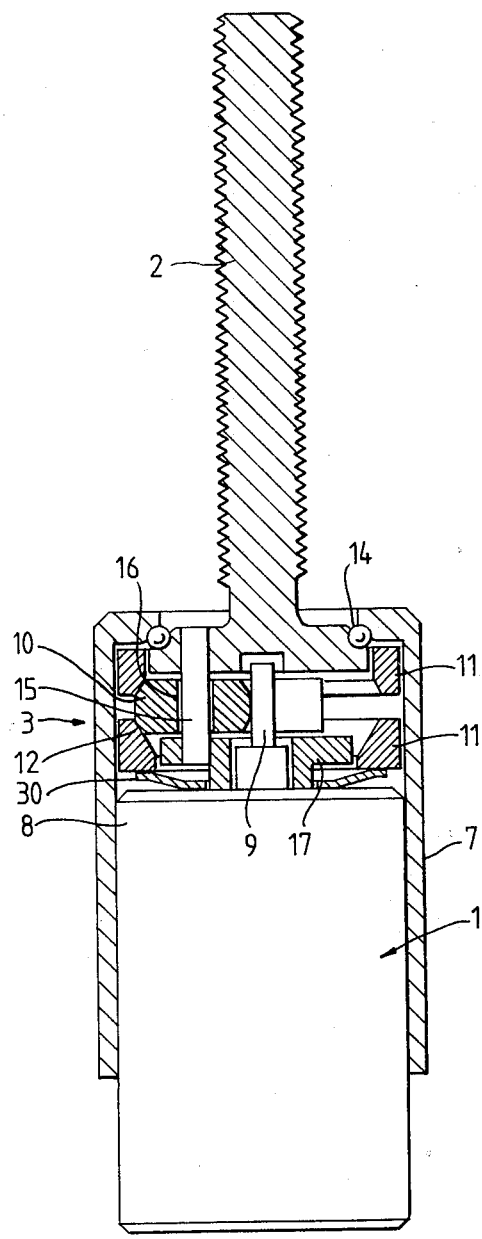
FIG. 1 is a sectional view showing an electric motor driving an output shaft by way of a clutch.
Figure 2:
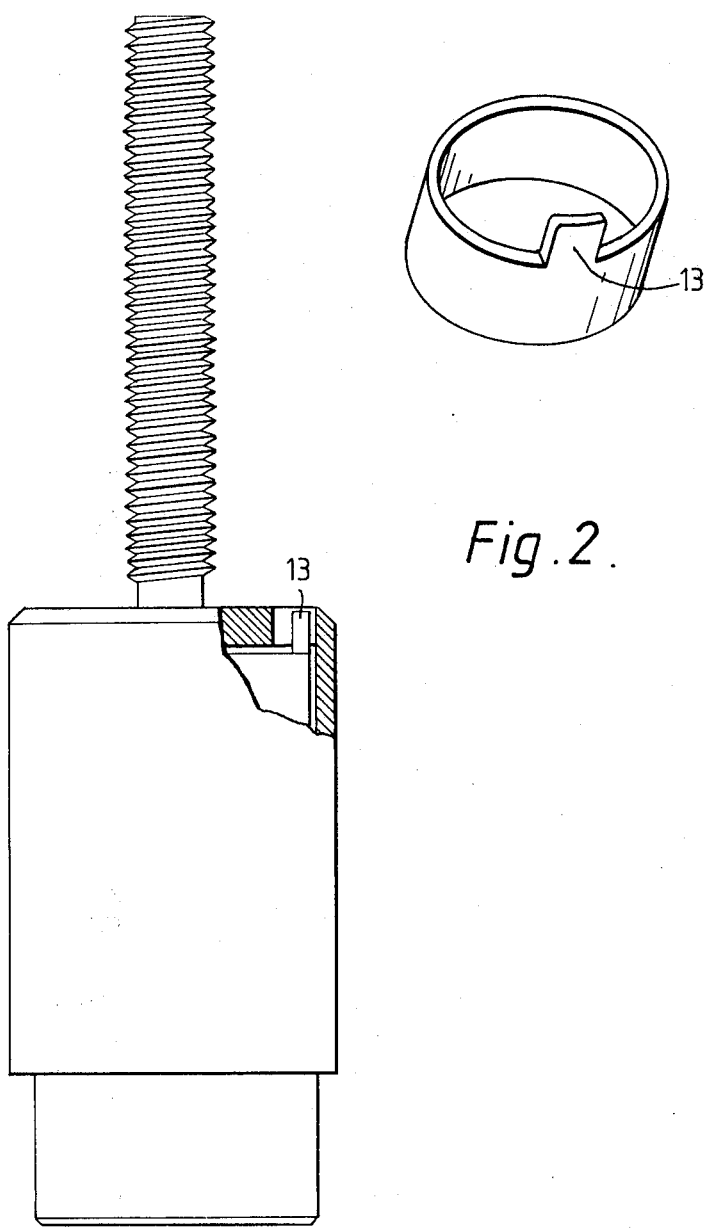
FIG. 2 is a partly sectional view of the arrangement of FIG. 1 showing a detail of the clutch.
Figure 3A:
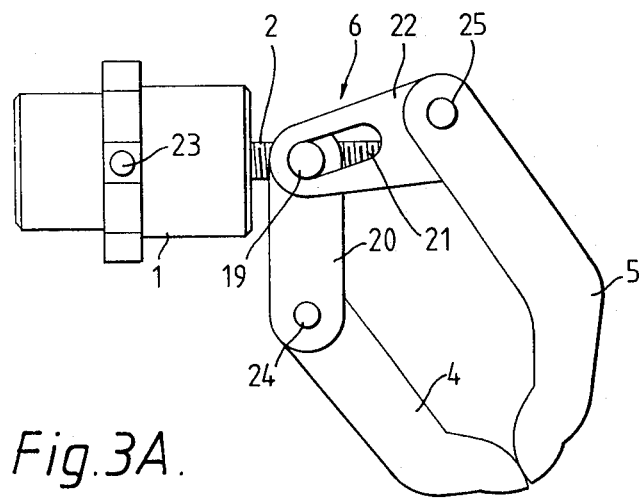
FIGS. 3A and 3B are a side view and a plan view respectively showing the motor of FIG. 1 connected to drive a pair of pivotal gripper members of a mechanical hand, a casing of the hand being omitted for clarity.
Figure 3B:
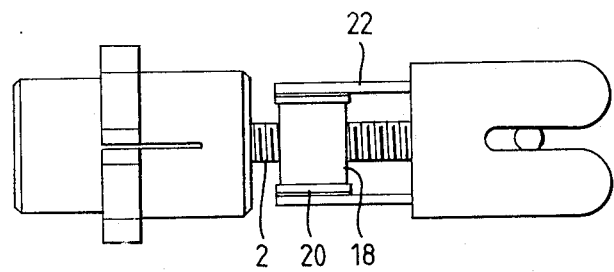
Figure 4A:
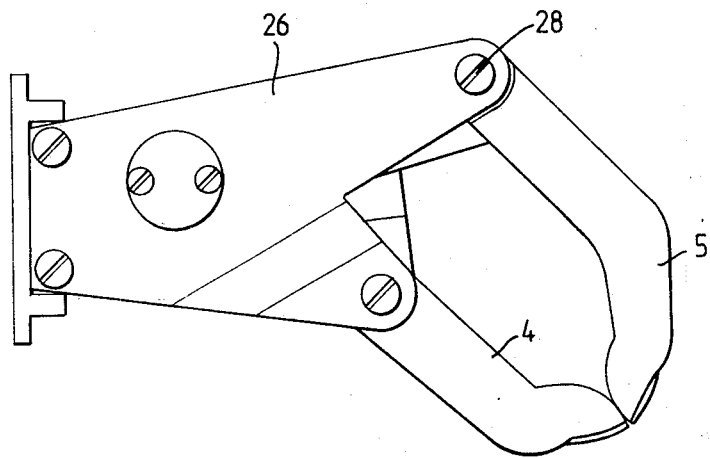
FIGS. 4A and 4B are views similar to FIGS. 3A and 3B, but showing the casing place.
Figure 4B:
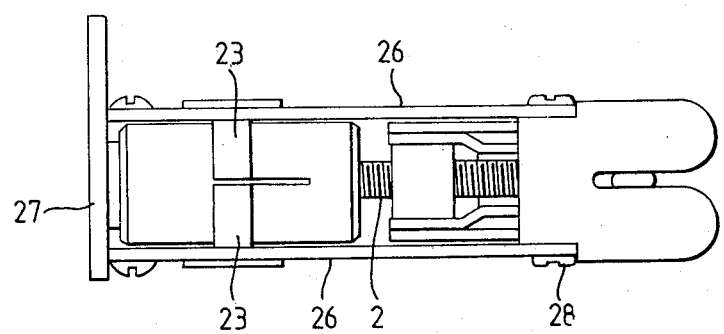

FIGS. 1 to 4 show a prosthesis comprised by a mechanical hand. As shown in FIG. 1, the prosthesis includes an electric motor 1 which drives an output shaft 2 by way of a clutch 3. As shown in FIGS. 3 and 4 the output shaft 2 is arranged to drive gripping members 4 and 5 in an opening and closing movement 1, a cover 7 is fitted non-rotatably over one end of a casing 8 of the motor 1. A part of this cover 7 serves as a housing for the clutch 3 and also serves to rotatably mount the output shaft 2. The motor has a main shaft 9 surrounded by three planetary rollers 10, which run in between two annulae 11. These rollers 10 may be made, for example, of an elastomeric material. The lower annulus 11 is biased upwardly towards the upper annulus by means of a spring disc 30, and co-operating tapered surfaces 12 provided on the annulae and on the rollers serve to urge the rollers 10 radially inwardly against the motor main shaft 9, whereby when the main shaft rotates, it frictionally urges the rollers 10 to rotate. The upper annulus 11 is prevented from rotating by means of a lug 13 (FIG. 2) projecting from it, the lug engaging in an opening in the cover 7. Thus, when the rollers 10 are frictionally urged to rotate by the main motor shaft 9, the rollers run around the inside of the stationary annulae 11. The output shaft 2 is externally screw-threaded, is rotatably mounted in a combined thrust and radial bearing 14, and is driven to rotate by three pins 15, one of which is shown in FIG. 1. Each pin is located through a centre bore 16 of its associated planetary roller 10, and is held captive at the rear in an aperture in a back thrust plate 17. It will be appreciated that if there is very high resistance to rotation of the output shaft 2, as would happen when the members 4, 5 close on an object, the main shaft 9 will slip against the rollers 10 so that the friction clutch will slip and there will be no drive.

However, if an electronic current limit device is used in the power supply circuit to the motor 1, i.e. a device for terminating the power supply to the motor before a 'stall' situation occurs, then this renders the slipping clutch 3 unnecessary.

The output shaft 2 with its 'Acme' type thread, has a nut 18 threaded on it, which nut is in the form of a trunnion, having a pair of projecting journals 19. These journals 19 allow the nut 18 to pivot within the yoke formed by the two "thumb"-operating levers 20, and the ends of the journals 19 protrude beyond the levers 20 to engage in slots 21 in two "finger"-operating levers 22. The drive unit comprised by the motor 1, clutch 3, and output shaft 2 is mounted in a pivot 23 on a chassis described below. This allows the shaft 2 to follow the arc path of the nut 18 around the pivot mounting 24 of the thumb member 4.

When the electric motor is energised to rotate the shaft 2 in a direction that draws the nut 18 towards the motor, the finger- and thumb-operating levers 20,22 are moved about their pivot points 24 and 25 thus causing a closing action of the finger and thumb, the geometrical layout of the unit providing the hand with a high pinch force, maintained after termination of power supply to the motor by the self-locking action of the shaft 2 and nut 18. It will be understood that the finger-operating levers 22 are pivoted by the journals 19 which serve as drive pins.

The hand is opened by reversing the direction of rotation of the electric motor, causing the shaft 2 to push the nut 18 away from the motor, the finger and thumb levers 22,20 being moved about their pivot points 25, 24, thus parting the fingers and thumb.

A 'maximum hand opening stop' may be comprised by an electric circuit breaker (not shown) which is mechanically operated by the pivoting action of the drive unit at the maximum opening stage. This terminates the power supply to the electric motor, thus avoiding the unnecessary waste of power which would otherwise be used, driving against a mechanical stop.

As shown in FIG. 4, the working parts of the hand and of the drive unit, are located between two chassis side plates 26 which are attached to off-set locations on a wrist plate 27. By turning the wrist plate through 180° the hand is converted from left to right or vice versa.

The finger and thumb pivot mountings 24,25 are held in position by headed screws 28 which pass through thread clearance holes in the chassis side plates 26 and are screwed tight into tapped sections at each end of the mountings.

The drive unit pivots on the pivot 23, the pivot 23 comprising stub journals mounted one on each of the chassis side plates. The stub journals project into two integral bores in the drive unit.

The complete unit is covered with a flexible inner glove which provides shape and body to an outer cosmetic glove which is fitted over the inner glove. The drive arrangement described has low mass, and will be very responsive in use.

The control circuit shown in the accompanying FIG. 5 has been developed particularly to provide continuous, variable speed control of the electric motor actuated prosthesis of FIGS. 1-4, but it will be appreciated that the system and portions thereof may be used, possibly with modification, in many other applications. The circuit is arranged to control the actual position of the gripping members 4 and 5. The circuit operates in "closed loop mode" whereby a personally-operable transducer element can be varied or set to select the desired "position" of the mechanical hand, i.e. select the desired spacing between the gripping members of the mechanical hand. A second transducer element (or feedback transducer element) senses the actual position of the hand, and this transducer element is automatically varied as the hand "moves", i.e. as the gripping members approach one another or separate from one another. The hand will thus be moved until it achieves the selected position. The transducer elements will normally be separate transducers, but as will be described below, the two transducer elements could from two parts of a single transducer.

The circuit includes, as transducers, two inductors $L_1$ and $L_2$ both of variable inductance. The inductance of inductor $L_1$ is variable personally by the user of the mechanical hand to select a desired position of the hand, while the inductance of inductor $L_2$ is varied automatically as the hand moves, there being a mechanical link between the hand-operating motor M and the inductor. Thus, for each position of the mechanical hand, there is a corresponding unique value of the inductance of inductor $L_2$.

The inductors $L_1$ and $L_2$ are connected in series with each other in a resonant circuit including a fixed capacitance so that, by varying the total inductance of the two inductors, the frequency of this resonant circuit is changed. The capacitor of the resonant circuit is not shown, but is incorporated in an oscillator circuit 100. Accordingly, by personally varying the inductance of inductor $L_1$, the user frequency modulates the output from oscillator circuit 100, a reduction in the inductance of inductor $L_1$ increasing the output frequency from the oscillator circuit, and vice versa. The output from the oscillator 100 is fed via line 101 to a demodulator 102 (to be described in more detail below) in which the signal is demodulated to produce an output voltage representative of the sum of the inductances of inductors $L_1$ and $L_2$.

This output voltage from the demodulator is fed via a line 103 to a D.C. amplifier 104 which compares the voltage output from the demodulator 102 with a reference voltage fed to the amplifier 104 by a line 105. If the inductance of inductors $L_1$ and $L_2$ is equal to a certain predetermined value, then the output voltage from the demodulator on line 103 is equal to the reference voltage on line 105 and, in effect, there is then no output from the amplifier 104. The sum of the inductances will be equal to this predetermined value when the selected and actual positions of the hand are the same. If, however, the sum of the inductances is higher or lower than this predetermined value, then the output voltage on line 103 will be higher or lower than the reference voltage. This difference in voltage will be amplified and fed along line 106 from the device 104 both to a pulse width modulator 108 (via a full wave rectifier 107), and also to a comparator 109.

The purpose of the device 108 is to generate a train of pulses for driving the motor M of the mechanised hand. If the output from the demodulator 102 (on line 103) is at a voltage much higher or lower than the reference voltage on line 105, then the output from the amplifier 104 will be a strong signal and it will cause the width of pulses emitted from the device 108 to be increased to drive the motor M at a high speed, whereas if the voltage difference on lines 103 and 105 is small, the signal on line 106 will be weaker and will cause the device 108 to emit motor drive pulses which are reduced in width to drive the motor M at a low speed. The rectifier 107 ensures that the signal fed to the device 108 is of the correct polarity.

The comparator 109 compares the voltage on line 106 with a reference voltage on line 110 and thus, in effect, senses whether the voltage on line 103 is higher or lower than the reference voltage on line 105. The output from the comparator determines the direction in which the motor M is driven, control of the motor direction being achieved by way of AND gates 111 and 112. Both AND gates receive one of their inputs from the pulse width modulator 108 by way of line 113. The gate 112 receives another input direct from the output of the comparator 109 on line 114, whereas the gate 111 receives an input from the comparator by way of an inverter 115.

It will be understood that the direction in which the motor M is driven will depend upon which one of the gates 111 and 112 is enabled, and this in turn will depend on the output from the comparator 109. This matter output in turn depends on the signal from the demodulator 102. Both of the AND gates may also receive a further input, although only the input to gate 112 on line 116 is shown. The purpose of these further inputs will be explained below.

Operation of the mechanical hand is closed loop mode will now be described. The system tends to restore itself always to a position in which the sum of the inductances of inductors $L_1$ and $L_2$ is equal to a certain predetermined value. Let is be supposed that the sum of the inductances does equal this certain value. In that case the output voltage fed from the demodulator 102 to the device 104 is equal to the reference voltage fed to the device 104 and, effectively, there is no output from the device 104 so that the motor M is not driven. If, now, the user wishes to open or close the hand, he operates the inductor $L_1$ to change its inductance and thereby select a new position for the mechanical hand. By changing the inductance of inductor $L_1$, the user changes the frequency output from the oscillator 100. This will cause the voltage output from demodulator 102 to move above or below the reference voltage fed to the amplifier 104. This will produce an output signal on line 106. The strength of the signal on line 106 will depend on how much the user has changed the inductance of inductor $L_1$, and the polarity of the signal will depend on whether the user has increased or decreased the inductance. The device 108 will then produce a train of pulses which will drive the motor. The direction of drive, controlled by the comparator 109 and the gates 111 and 112, will depend upon whether the user has increased or decreased the inductance of inductor $L_1$. As the motor M drives the mechanical hand towards its selected position, the mechanical link between the motor M and the inductor $L_2$ will change the inductance of $L_2$ in a sense to tend to restore the sum of the inductances to the said predetermined value.

During the initial movement of the motor M, the signal on line 106 will be relatively strong, and the pulses driving the motor will be very wide to drive the motor relatively quickly. However, as the motor moves the hand towards its selected position, the sum of the inductances of inductors $L_1$ and $L_2$ will approach the predetermined value, the signal on line 106 will become weaker, and the width of the pulses driving the motor will decrease to drive the motor slower. Movement of the motor and hand will effectively cease when the sum of the inductances equals the predetermined value, at which time the hand will have reached its selected position.

The mechanical hand shown in FIGS. 1–4 is provided with a slipping clutch 3 and also with a circuit breaker (not shown) to break the electric circuit to the drive motor when the hand reaches its "fully open" position. However, these devices can be dispensed with, and can be replaced by any suitable electronic device to switch off the motor when its stalls, i.e. when it can no longer move because the hand is fully open, fully closed, or has closed on an object. When the motor stalls, its current consumption increases, and this increase in current consumption can be used to switch the motor off. One way of achieving this is to provide additional inputs to both AND gates, such as the input 116. The input to the AND gates will be interrupted when the motor stalls to disable both gates.

The inductors $L_1$ and $L_2$ may comprise ferrous or ferrite cores movable inside coils. The coils may be provided with internal plastics material sleeves to provide a low friction bearing for the cores. The core of inductor $L_1$ can be moved, for example, by means of a personally operable pull cord attached to the core, and a spring may be provided to urge the core towards an end position thereof. Alternatively, the inductor $L_1$ could be arranged to be varied by the turning of a knob. The mechanical link between the motor M and the core of $L_2$ can take any suitable form, and the link could instead extend between the mechanical hand and the motor.

The demodulator device 102 can take any convenient form, but it is presently preferred to use a mono stable (triggered by the oscillator) of preset time duration, and to integrate these pulses so as to produce a D.C. level proportional to the oscillator frequency. This demodulated signal is buffered and fed to the D.C. amplifier 104. Since the system relies on sensing and comparing frequencies, extraneous amplitude modulated signals do not effect circuit operation. In fact very long unscreened leads can be used to connect the coils of the inductors $L_1$ and $L_2$ to the oscillator 100. Any stray capacitance is swamped by the resonant capacitor of approximately 47,000 pf, this resonant capacitor being the capacitor in parallel with the inductor coils which provides the resonant circuit.

One prototype mechanical hand operating system has operated satisfactorily with 3 meter lead lengths with the oscillator 100 running at 15 KHz. Further, since one side of one of the coils is at ground potential, only one wire is needed to carry the modulated information from the oscillator 100.

The system can be used not only for driving a mechanical hand, but also in remote position measurement systems, with reasonable accuracy.

It is possible to modify the circuit to operate in "open loop" mode. In open loop mode the user will personally actuate a control device to energise the hand drive motor, and the motor will continue to operate for as long as the control is held actuated by the user. To modify the circuit for open loop operation, it is merely necessary to replace the inductor $L_2$ (which may be regarded as a feed-back inductor) by a short circuit and to remove the mechanical link. In this case the core of inductor $L_1$ can be moved in a sense to close or open the hand, open-loop gain would have to be reduced to provide a usable control.

For operation in closed loop mode, the inducator $L_1$ can be replaced by some means which will have the same effect on the system as the inducator $L_1$. For example, the oscillator in the I.C. of the demodulator 102 could be driven by a voltage control signal supplied via line 117, which signal could be derived from a unit operated, for example by muscle contraction or by electromyograph signals. In this case, the position of the hand would be a function of the input voltage applied to the oscillator of the demodulation I.C.

One slight problem with the arrangement shown in FIG. 6 is that the relationship between movement of the core and movement of the hand will not be linear if the inductors are identical. One way of minimising the non-linearity would be to use long coils and to rely on small core travel, while another method would be to replace the inductors $L_1$ and $L_2$ by a single inductor. In this case, one of the coil and the core would be personally moveable, and the other of the coil and the core would be movable by the mechanical links.

For driving the motor M, it is desirable to use a drive package 118 between the AND gates and the motor, the drive package serving to amplify the pulses from the device 108.

The circuit of FIG. 5 uses capacitors as transducers, and this has been found to be an accurate, compact, and reliable design. However, it would be possible to use resistors as transducers instead.

In this case the circuit arrangement would be similar to that of FIG. 5, but would be somewhat simpler. FIG. 6 shows only that part of a resistive transducer circuit which will differ from the circuit of FIG. 5. In FIG. 6, two variable resistors (potentiometers) $R_1$ and $R_2$ are connected in series across a control voltage. The oscillator 100 and demodulator 102 of FIG. 5 are not used in the circuit of FIG. 6, and instead the line 103 which feeds the D.C. amplifier 104 is connected to a point 150 between the resistors $R_1$ and $R_2$. The circuit will operate in the same way as the circuit of FIG. 5, i.e. by personally varying the resistance of $R_1$, the user will alter the voltage at point 150, which voltage is compared with a reference voltage by the D.C. amplifier 104. The drive motor M of the mechanical hand will then drive the gripping members 4 and 5, and the resistance of the feedback resistor $R_2$ will be varied in a sense to restore the voltage at point 150 to the reference voltage.

It is possible to use capacitors as transducers, instead of inductors or resistors, as shown in the circuit of FIG. 7.1.

A low power proportional control system to be described with reference to FIGS. 7.1 to 7.8 has been developed particularly to provide continuous, variable speed control of an electric motor actuated prosthesis, but it will be appreciated that the system and portions thereof may be used possibly with modification, in many other applications. The system supplies a pulsed drive to the motor and speed control is achieved by varying the frequency of the pulses. Working in conjunction with the drive circuit described earlier, the control system is capable of the following two modes of operation:

(i) Open loop, unidirectional or bidirectional control either proportional or on-off action.

(ii) Closed loop control utilizing tansducer for input and feedback signals or operating directly from control voltages.

In the open loop mode, the control unit essentially functions as a speed control system. The direction of drive is controlled by two independent inputs to the system which are compatible with switching or proportional signal sources. This mode is expected to be of use in applications where a different degree of sensitivity of control is required depending on the direction of the drive.

In the closed loop mode the control system compares the signals present at two input channels. Depending on the magnitude and sign of the difference between these inputs, a drive of corresponding magnitude and direction is applied to the motor. If a transducer is attached to the prosthesis to derive signals corresponding to force or displacement, etc., and used as one of the inputs to the control system, the particular parameter chosen can be controlled under servo action. The parameter under control will be required to follow, via the transducer output, the signal present at the other input channel. This input may be derived from a variety of sources and may indeed be another transducer.

The basis of the proportional system is the particular method by which drive is applied to the motor. As mentioned earlier, this is achieved by a pulse technique whereby the speed of the motor is controlled by the frequency of the applied pulses. The pulses are of sufficient duration to cause a small movement of the prosthesis if applied singly. Hence, as frequency is increased, the resultant movement progresses from discrete steps through to continuous slewing. The method requires that the drive motor be a fast response type and that the inertia of the load is relatively small, but this is anyway a desirable characteristic for a prosthetic system component.

The advantages of the pulsed drive method for prosthetic control systems are, inter alia, as follows:

(i) The power consumption is low due in part to the fact that because of the finite step movements produced and the frequency proportional "error" response, the system does not "hunt" around small errors. In this condition the power consumption of the system is only due to the transducer conditioning and error detecting systems which is very low. Small errors result in low error-proportional frequencies which again result in low power consumption.

(ii) The system operates to ensure that the prosthesis is highly controllable. The discrete pulse drive method offers a number of unique characteristics which enhance the degree of control attainable. Even at low speeds, the movement is steady and positive due to the fact that full power is momentarily applied to the prosthesis motor. Static friction or breakaway forces are much more easily overcome by the pulsed drive and hence there is no apparent deadband as with linear drive systems. Furthermore, the range and controllability of gripping or stall forces is greatly enhanced. Thus the system is more tolerant of mechanical friction in the prosthesis, making for extended useful life and greater reliability of operation.

(iii) The method readily provides tactile feedback to the amputee. Under conditions in which the motor is stalled the pulsed drive is not smoothed out by inertial effects and sharper torque pulses are developed. The character of these pulses is modified by the specific properties of the mechanical load experienced by the prosthesis, and the frequency of repetition relays information to the amputee regarding the critical power consumption in the stall condition. Hence the amputee can gain information on certain mechanical properties of the load or gripped object, and can estimate the degree of grip enhancement obtained by pulsing the prosthesis in stall.

The preferred embodiment of the general low power proportional control system is comprised of the following six sub-systems:

(i) A pair low power differential capacitive transducers to provide input and feedback systems.
(ii) A transducer modulator and demodulator unit.
(iii) A differential output charge amplifier.
(iv) A proportional repetition rate pulse generator.
(v) A pulse steering and current limit shut-off circuit.
(vi) A bridge type bi-directional motor drive circuit.

Referring to the block diagram of FIG. 7.1, the system incorporates transducers respectively sensing the desired position (input) and the actual position (feedback) of the prosthesis and means for deriving therefrom a measure of the "error" between these two quantities which is to be diminished by energisation of the prosthesis motor in the appropriate sense. As will be described in detail below, there is derived in the system a binary signal indicative of the sign of this error. Transmitted on line A in the diagram is an analogue signal indicative of the magnitude of this error, transmitted on line B in FIG. 5.1. The analogue signals on line B are passed to the proportional repetition rate pulse generator which produces pulses of a predetermined width at a repetition frequency proportional to the magnitude of the error. This train of pulses is passed to the pulse steering and current limit shut-off stage, to which the signal on line B is also passed, and this stage applies a corresponding pulse train to either of two inputs of a drive circuit in accordance with the appropriate sense of motor rotation, the drive circuit applying corresponding voltage pulses to the motor M with a polarity depending upon the input to which the pulse train from the pulse steering and current limit shut-off stage is applied. The drive circuit also incorporates means for sensing the rise of the current supplied to motor M above a predetermined level and for supplying a corresponding signal to the pulse steering and current limit shut-off stage, the latter being operable to terminate the passage of pulses to the drive circuit on detecting a rise in motor current above the predetermined level. The control signals on lines A and B are shown in the block diagram originating from the transducer demodulator system. They can, however, be derived from an alternative source and used to control the system instead of the transducer signals. Thus, the sub-systems (iv), (v) and (vi) above comprise the basic proportional system and form the heart of the various configurations that can be achieved.

The transducer modulator/demodulator unit and the charge amplifier are specifically for use with lower power capacitive transducers when these devices are used in a particular application to provide input or feedback signals. When such transducers are used to provide both feedback and input signals, the outputs may be summed directly to produce the error signal. This is an extremely efficient configuration of the control system where the need for independent signal conditioning for the transducers is eliminated. With a single transducer system, the transducer is coupled in exactly the same manner to the charge amplifier as the common-output transducers. Being a charge balance system, the effective gain that the amplifier provides for each transducer is to a large extent independent of additional input capacitance.

Transducers are used in the low power control system to derive electrical signals relating to force and displacement. In either case the principle of operation of the devices is the same and, electrically, they are indistinguishable. The transducers are essentially three-plate capacitors where one of the electrodes (the output) are moveable. The capacitance between the moveable electrode and the other two plates is nominally equal but is unbalanced by the movement of the output plate. Differential drive voltages of equal magnitude are applied to the input plates and thus, when the capacitance between the moveable plate and the inputs is the same, the charge developed at the output is zero. As the moveable plate is displaced towards a particular input plate the capacitance between that plate and the output increases, and that between the output and the other plate decreases. Consequently, the charge balance is offset and a charge signal appears on the output plate. The magnitude of the signal is related to the displacement of the output plate from the null position, and the relative phase of the output signal is a function of the direction of the displacement.

The method employed for conditioning the transducer outputs, whether they are used singly or as a parallel connected pair, is that of charge amplification. The method is appropriate for use with capacitive signal sources, particularly where low level signals are involved since it is inherently insensitive to shunt or stray input capacitance.

This feature allows the use of very low capacitance transducers without loss of sensitivity and consistency of characteristic due to stray capacitive effects. Without the requirement for a highly capacitive source to drive the charge amplifier, the transducer can be made into a physically small and rugged device, the manufacturing tolerances and complexity can be reduced and, perhaps of most importance, the power consumption is low.

Referring to the circuit diagram 7.2, it can be seen that an operational amplifier OA1 is the active device in the charge balance system. Input current from the transducers is balanced via $C_2$ from the potentially divided output of OA1. Resistors $R_4$ and $R_5$ here are used in this potential divider configuration to provide additional gain from the front end current. Overall d.c. stability is provided by direct negative feedback via $R_6$, but this path is decoupled by $C_3$ and hence only represents input shunt resistance at the modulation frequency. $C_3$ is chosen so that the potential division effect of $R_4$, $R_5$ does not extend well below this frequency and hence provides the charge amplifier with a high pass input characteristic. The primary object here is to reduce the sensitivity of the charge amplifier to mains signals but an additional benefit is the reduction in total inherent noise produced by the front end. Capacitor $C_5$ decouples the non-inverting input of OA1 to prevent positive feedback effect from stray capacitive coupling to this input. $R_1$ and $R_2$ provide a half-rail reference voltage for establishing the quiescent output levels of OA1, OA2, and this reference is decoupled by $C_1$. Amplifier OA2 in conjunction with the feedback network $R_7$, $R_8$ functions as a unity gain inverter to provide balanced drive to the following demodulator stage.

As mentioned earlier, the transducers used in the low power control system are capacitive types. They are necessarily a.c. energized devices and, therefore, require an oscillatary source to drive them and an amplifier/demodulator unit to convert the outputs to d.c. levels. This is the function of the modulator/demodulator and the charge amplifier circuit.

The demodulator circuit produces two output signals: an analogue voltage ranging from OV to the +VE supply which is proportioned to the modulus of the magnitude of the a.c. input voltage, and a binary signal corresponding to the phase of the input voltage relative to the modulator outputs. This type of demodulation is required because of the characteristics of the frequency-proportional stage which follows the demodulator. Negative quantities cannot be expressed in terms of a frequency unless an off-set zero is used. This is undesirable from the point view of the systems discussed here in that, in the zero or quiescent state, the current drain of the control circuitry would not be a minimum.

Referring to the circuit diagram, FIG. 7.3 it will be seen that a single integrated circuit, IC3, connected as a free running astable multivibrator, provides the modulation signals Q and $\overline{Q}$ to drive the transducers. The modulation signals swing between the supply rails, and for the particular IC chosen, the waveforms are perfectly symmetrical due to an internal divide-by-two function. The modulator outputs are also routed internally in the circuit via a quad analogue switch IC2 to the gating inputs of another switch, IC1. IC2 is controlled by comparator OA1' such that the phase of two of the gating voltage inputs to IC1 can be reversed. IC1 functions as a balanced synchronous demodulator or lock-on detector. The circuit switches the inputs to two low pass filters R4, C2 and R6, C3 (connected to inputs of amplifiers OA1' and OA2' respectively) alternately between the complementary input signals $e_o$ and $\overline{e}_o$ from the charge amplifier. By this method, all non-coherent signals (not coherent in frequency and phase) are averaged out, and the component of the synchronous frequency present at the input appears as a d.c. signal at the output of the low-pass filters. OA1' functions as a high gain comparator detecting the sign of the demodulated output. The section of the switching detector feeding OA1' is directly coupled to the modulating voltages Q and $\overline{Q}$, and therefore yields an output containing information on the phase of the input signals. The reference input for OA1' is derived from the input signals $e_o$ and $\overline{e}_o$ after averaging and decoupling by R1, R2 and C1. For the switching demodulator part feeding OA2', the phase of the gating voltages is reversed according to the output state of OA1'. Since it is the relative phase of the gating voltages with respect to the input signals that determines the sign of the demodulated output it will be realised that the output of the demodulator part feeding R6, C3 is stripped of directional information. The input to OA2' is of d.c. level which, in the quiescent state, is equal to the mean of the d.c. components of the inputs $e_o$, $\overline{e}_o$. In the presence of a synchronous input, the voltage applied to OA2' increases in a positive direction proportional to the magnitude of the a.c. signal. OA2' in conjunction with PNP transistor TR1 connected in a common emitter mode forms a non inverting amplifier/buffer circuit. The quiescent output is biassed to near OV potential by the filtered input via R6, and the potential divider R7, R9 and R11. The use of the common emitter PNP output stage allows for a high current "pull-up" type of output with the ability to swing virtually between the power rails for grounded loads.

The function of the proportional repetition rate pulse generator is to generate pulses of constant duration at a rate proportional to the magnitude of the d.c. analogue control voltage. As mentioned previously, the duration of the pulse is that which applied singly to the output stage will cause a discrete but small movement of the prosthesis. To achieve proportional control the frequency of these pulses is varied from zero to the point where they merge to form a sustained input to the drive circuit. In order to achieve compatibility with existing commercially available prosthetic control devices, the range of analogue control input was chosen to be the supply voltage, and thus at 0V applied to the input, the output pulses do not occur and at the +Ve rail potential the pulses are merged. The exact constant of proportionality or the "gain" of the converter (the ratio of output frequency to input voltage) is different depending on the function to which the overall system is applied. In the open loop mode the amputee controls the speed of drive of the prosthesis by varying the input from a sensory device such as a cord force transducer or a myo-electric amplifier. Here, the point of merging of the output pulses would be adjusted to suit the individual. The level of input desired to produce full output would be determined by experiment. In the closed loop mode, however, the converter requires a high gain in order to achieve accuracy or responsiveness of the control system. This is so because the input and feedback variables are differenced to produce two drive signals. For good accuracy and high resolution the error must be small and, correspondingly, requires higher amplification in the control loop.

Referring to the circuit diagram of FIG. 7.4 the voltage to frequency conversion is performed by IC1. This circuit is a micropower phase-locked loop and only the VCO (voltage controlled oscillator) section is used. The constant of proportionality of the stage is determined by the timing components R1, C1. The frequency for a given input voltage is inversely proportional to both of these components, and can be pre-set over a very wide range. The square wave output of IC1 is capacitiviely coupled to the monostable multivibrator IC2. Here, the timing components R2, C2 determine the duration of the output pulse from the circuit.

The pulse steering and current limit shut off circuit performs the following functions:

(i) It directs the frequency-proportional drive to one of the two inputs of the drive circuit, and
(ii) It provides a latch-out function to isolate the drive pulses from the selected input to the drive circuit in response to a current limit overload condition.

The pulse steering and current limit shut-off circuit may take a variety of forms. One such form is illustrated in FIG. 7.5. It will be seen from the schematic diagram shown in FIG. 5.5 that the selector or pulse steering circuit comprises 'NAND' gates IC1A, IC1B and IC1C. The control input signal from OA1 (FIG. 7.3) which indicates the sense in which the motor is to be driven is fed directly to one input of gate IC1C and also to IC1A which supplies an inverted signal to one input of gate IC1B. The pulse train provided at the output of IC4 (FIG. 7.4) is applied to the other input of gate IC1B and to the other input of gate IC1C in FIG. 1, and is thus routed to the output of gate IC1B or IC1C depending on the signal from DA1 (FIG. 7.5). More particularly, this pulse train is routed to the output of IC1B if the desired sense of motor rotation is such as to open the hand and is routed to the output of IC1C if the desired sense of rotation is such as to close the hand.

The output of IC1B is connected directly to the input of the drive circuit (described below) at which signals are applied to rotate the motor in the sense to open the hand, whereas the output of IC1C is connected to the input of the drive circuit at which the signals are applied to rotate the motor in the sense to close the hand, via a gating circuit. This gating circuit is formed by NAND gates IC2A and IC2B and prevents the drive pulses reaching the "close" input to the drive circuit if the output of a latch comprising gates IC2C, IC2D is high. The logic level of the output of latch circuit IC2C, IC2D is determined by a d.c. signal derived from a current limit output of the drive circuit. In the proportional or pulsed drive mode, the current limit signal is a succession of positive going pulses. These pulses are fed via a diode pump D1, R1 to a filter circuit C1, R2. If the mean amplitude of the current limit signal formed by the train of such pulses fed to the diode D1 exceed a certain value, the d.c. output of the pump/filter circuit exceeds the threshold voltage of the latch and the output of IC2C is set, thereby preventing the passage of pulses to the 'close' output.

To reset the latch, the direction of the error signal must be reversed, e.g. by supplying a command to open the hand. In this situation the reset input of the latch is taken high by the pulsed drive output available from IC1B.

As will be apparent from the following description, the current limit signal is a measure of the load applied to the motor, and as the motor is more likely to be overloaded when the gripping members of the hand grips an item than when the hand is merely opened, e.g. to release an item, a current limit control facility may not be required for the 'hand-opening' mode. However, such a facility may be provided for the latter mode in the same way as described for the 'hand-opening' mode. A variant of the circuit of FIG. 7.5 is shown in FIG. 7.6. This variant is specifically designed for use in conjuction with the drive circuit of FIG. 7.7, and for ease of understanding, this drive circuit will be described first.

Referring to the circuit diagram shown in FIG. 7.7, transistors TR8, TR9, TR10 and TR11 form a bridge configuration allowing for the load (the motor) to be connected in either polarity across the supply via switching means formed by these transistors. Transistors TR12 and TR13 are n-channel enhancement mode VMOS devices which conveniently and directly provide low-power, logic-compatible inputs to the bridge. These devices are arranged such that, upon saturating, a single resistor R16 or R17 provides base current drive to the relevant complementary pair of the bridge transistors. Dynamic braking is achieved by taking both inputs to logic 1 (the input terminals of TR12, TR13 to the positive supply rail). In this state the transistors TR7 and TR14 are both turned on. These transistors divert the base current drive to the upper bridge transistors TR8, TR9 and hence prevent them from turning on. In this condition the lower two bridge transistors TR10, TR11 are on, and a short circuit is formed across the load. Depending on the polarity of the EMF produced by the load at the point of braking, the load current flows either through the loop formed by TR10 and D4 or through TR11 and D3. To prevent damage from Inductive kick-back effects, a freewheeling diode network D1–D4 is incorporated into the package. The circuit shown in FIG. 5.7 also includes a current limit threshold circuit.

The current limit threshold circuit comprises the transistors TR1 to TR6 and the associated circuitry. Transistors TR1 to TR4 are part of a NPN transistor array in an integrated circuit, and their matched characteristics are utilized in an emitter coupled differential amplifier circuit with darlington pair inputs. The differential amplifier senses the voltage drop in a current sensing resistor connected externally between the driver stage positive supply line S and the positive supply line T via which line S is energised and which is at a higher positive voltage than line S. This sensing resistor in turn senses the current in the positive supply rail to the output (i.e. driving) stage. The voltage across the current sensing resistor is compared with the potential across R3. When the current supply to line S increases to the point where the base of TR4 is taken more negative than the base of TR1, TR6 conducts producing a current-limit output signal in the form of a positive voltage signal across R1/R4. This signal is provided as an output appearing at pin E on the circuit to be described with reference to FIG. 7.6. Positive feedback is provided via R2 in order to provide a fast response and to introduce a small amount of hysterysis into the threshold characteristic of the circuit.

A minimum threshold trigger level is preset within the circuit by the potential divider action of R3, R2 and R4, which in the absence of any external threshold level adjustment determines the voltage applied to the base of TR1. The threshold or triggering point can be externally increased by injecting current into the junction of R3, R2 (pin α) from a more negative potential. (The junction of R3, R2 is almost at the positive supply potential).

With the programming terminal pin α floating, the triggering potential for the differential amplifier is given approximately by:

$$V_L = V_{DD} \frac{R_3}{R_2} \quad (R_2 \gg R_3, R_2 \gg R_4) \quad (1)$$

and the corresponding threshold current is:

$$I_L = V_{DD} \frac{R_3}{R_2} \cdot \frac{1}{R_3} \quad (2)$$

with current $I_p$ flowing into the programming terminal the threshold current is given by $$I_L = \left\{ \frac{V_{DD}}{R_2} + I_p \right\} \frac{R_3}{R \text{ sense}} \quad (3)$$

In the above, R sence is the said resistor connected between S and T. As a result of the positive feedback action of the circuit, the turn-off threshold current is less than the trigger current is less than the trigger current. The difference is the current:

$$I_{diff} = \frac{R_1}{(R_1 + R_4)} \cdot \frac{R_3}{R_2} \cdot \frac{V_{DD}}{R \text{ sense}} \quad (4)$$

The trigger threshold can be controlled either from a current source or via a series resistor from a control voltage. A simple manual method of programming is shown in FIG. 5.8 where the control current is derived from potentiometer VRA and resistor RB.

The control circuit shown in FIG. 5.6 embodies the following features:

(i) Current limit shut-off control with pulsed override feature.

(ii) Automatic Dynamic braking facility.

The circuit of FIG. 7.6 includes output N and P respectively, for connection with inputs A and B respectively in FIG. 5.7, and has inputs C and H at which pulses are applied respectively to secure the application of pulses at the outputs N and P. The inputs C and H are respective inputs of respective two-input Schmitt NAND gates IC1A and IC1C each of which has its other input forming a respective gating input B or H respectively of the circuit. It will be apparent to those skilled in the art that appropriate input pulses for the circuit of FIG. 5.6 may be derived in various ways from the circuit of FIGS. 5.3 and 5.4, for example by connecting the inputs C and W in a "wire OR" configuration to the output of IC2 in FIG. 5.4 and connecting the output of OA1 in FIG. 5.3 directly to input B and via an inverter to input G. It will be seen from FIG. 5.6 that the passage of the input signals to inputs C and H through the circuit to outputs N and P is controlled by a number of input signals. In addition, the unit controls the outputs in such a manner as to initiate dynamic braking following the end of a "drive" command.

Current limit shut-off control is achieved by means of the latches IC5A, IC2A and IC5B, IC2B and the monostable multivibrator IC4A. Upon receiving a drive command (either "drive A" or "drive B" input) i.e. either a pulse received from gate IC1A or a pulse from gate IC1C via gate IC1B respectively, the monostable multivator is triggered. The Q output is used to drive the IC5A, IC5B outputs of the latches low. Under normal start-up conditions a current limit signal will occur but, provided it does not last for longer than the override pulse T₁ the outputs of IC5A, IC5B will remain low. In this state, the inverted drive signals from IC1A and IC1C are gated through IC2C and IC2D. Should a current limit signal occur without an overlapping pulse T₁, the outputs of IC5A IC5B go high and the drive signals are inhibited. This is the current limit shut-off function. If the input causing the current limit condition is removed and re-applied so as to initiate another T₁ pulse, the current limit shut-off can be temporarily overridden and the load i.e. motor driven for a further duration. Obviously, under stall conditions, the current limit signal will quickly appear and re-inhibit the drive at the end of the override interval.

The second monostable multivibrator IC4B is used to initiate a dynamic brake interval following a drive command. As mentioned earlier, dynamic braking is initiated in the drive circuit by taking both inputs high. The inverted drive signals from IC3A, IC3B are injected into IC3C and IC3D in the negative logic OR sense together with the dynamic brake pulse from the Q output of IC4B.

The Schmitt Nand Gate ICI is used to provide sharp triggering edges to the monostable multivibrators IC4A, IC4B and to follow the anti-bounce input circits. These input circuits provide a short lag response in order to prevent unwanted operation of the dynamic brake function. This would occur if the drive signals were corrupted by contact-splash or glitch noise.

The drive and control system described with reference to FIGS. 7.1 to 7.8 in combination essentially form a drive and control system for loads such as motors, solenoids and other electromechanical devices. In addition, the system would by useful in general power drive switching applications. The system operates in a switching mode and is fully reversible. Hence the effect is that the load is efficiently switched across the supply in a direction determined by the input signals to the system.

The drive circuit described with reference to FIG. 7.7 has the advantage of providing a symmetrical and fully reversible drive characteristic, using an efficient, low saturation voltage design. The drive circuit has a very low standby drain current, and affords compatible with inputs standard logic I.C.s with the operating modes of the circuit being selected by the binary signals on the inputs. Four modes of operation are afforded, viz: drive forward, drive reverse, off and dynamic brake. The circuit incorporated a current limit threshold facility with programmable input and an output compatible with standard logic I.C.s for feedback and control purposes. The circuit allows a reliable, compact and extremely flexible configuration to be adapted—allowing easy system design, high system component density and efficient heat dissipation. It has been found possible to incorporate the circuits described in an O.E.M. thick film motor control package to industry.

Whilst the system described will normally be operated in the proportional control mode, where this is possible for the amputee, it will be appreciated that the system may, if desired, be operated with a simple on/off action, simply, for example, by applying an appropriate continuous signal to the respective input, e.g. input C or B in FIG. 7.6, by way of an appropriate switch arrangement (not shown).

We claim:

1. A prosthesis comprising:
  (a) a gripping member;
  (b) an operating lever mounted to pivot about a pivot axis and operatively connected to the gripping member;
  (c) a power unit including an electric motor, and a drive shaft rotatable by said electric motor;
  (d) means connecting the drive shaft to the operating lever at a region spaced from the said pivot axis of the operating lever, said connecting means being constructed so that when the drive shaft rotates the connecting means (and also the region of the operating lever connected to the shaft) travels axially along the shaft thereby causing the operating lever to pivot about its pivot axis; and
  (e) means pivotally mounting said power unit to allow the connecting means to move along an arcuate path about the pivot axis during pivoting of the operating lever.

2. A prosthesis as claimed in claim 1, in which the connecting means comprises a nut which is screw threaded on the drive shaft.

3. A prosthesis as claimed in claim 1, in which the operating lever is integral with, or directly connected to, the gripping member.

4. A prosthesis as claimed in claim 1, further including a second gripping member which co-operates with the first mentioned gripping member for gripping an object, said second gripping member being pivotally mounted and being driven in its pivoting movement by rotation of said drive shaft.

5. A prosthesis as claimed in claim 4, in which said second gripping member is pivotable by a further operating lever formed with a slot in it, and in which a drive pin for pivoting the second gripping member is engaged in the slot, and is moved axially of the drive shaft by rotation of said drive shaft.

6. A prosthesis as claimed in claim 5, in which the connecting means comprises a nut which is screw-threaded on said drive shaft, and in which said drive pin is mounted on said nut or on said first mentioned operating lever.

7. In, or for, a prosthesis according to claim 1, a servo control system in which a motor is used to move a movable member, the system having first and second variable transducers comprised by two inductors, two resistors, or two capacitors, the first transducer being personally variable to effect energisation of the motor to move the movable member, the value at which the first variable transducer is set determining a desired position to which the movable member is to be moved, the second transducer being drivingly connected with the movable member so that the second inductor is varied as the movable member moves, the two transducers being part of a closed-loop control circuit which, in response to a change of value of the personally-variable transducer, drives the motor a sense to vary the value of the second transducer in a sense to tend to restore the sum of the values of the transducers to a predetermined value.

8. A servo control system as claimed in claim 7, and further comprising an oscillator circuit, a change in the value of the personally-variable transducer serving to frequency-modulate the oscillator circuit.

9. A servo control system as claimed in claim 8, and further comprising means to demodulate the modulated output of the oscillator circuit whereby to produce a demodulated signal, the demodulated signal being used to drive the motor.

10. A servo control system as claimed in claim 9, and further including means to derive, from said demodulated signal, a train of pulses for driving the motor, the duty cycle of the pulse train depending on the amount by which the total value of the two transducers deviates from the predetermined value.

11. A servo control system as claimed in claim 9, and further including a comparator arranged to compare the demodulated signal with a reference voltage, and to gate the motor drive pulses, for determining the direction of drive of the motor, according to whether the demodulated signal is at a higher level or a lower level than the reference voltage.

12. A servo control system as claimed in claim 11, and further including an amplifier to amplify the demodulated signal before feeding it to the comparator.

13. A servo control system according to claim 7, in which the transducers are inductors.

14. A servo control system according to claim 7, in which the transducers are resistors.

15. A servo control system according to claim 7, in which the transducers are capacitors.

16. A servo control system according to claim 13, in which the inductors comprise cores movable within coils.

17. A prosthesis as claimed in claim 1 including a servo control system in which a motor is used to move a movable member, the system having an inductor the inductance of which is variable to effect energisation of the motor to move the movable member.

18. A prosthesis as claimed in claim 1 including a servo control system in which a motor is used to move a movable member, the system having an inductor the inductance of which is arranged to vary as the movable member moves whereby to provide a feedback signal indicative of the position of the movable member.

19. A prosthesis as claimed in claim 1 including a servo control system in which a motor is used to move a movable member, the system having a first inductor and a second inductor, wherein the first inductor is personally variable to select a desired position of the movable member, and the second inductor is drivingly connected with the movable member whereby the inductance of the second inductor varies as the movable member moves.

20. A prosthesis as claimed in claim 1 including a servo control system in which a motor is used to move a movable member, wherein the servo control system comprises a single inductor the inductance of which is variable to effect energisation of the motor to move the movable member and also to provide a feedback signal indicative of the position of the movable member.

21. A prosthesis as claimed in claim 20, wherein the single inductor comprises an inner portion extending into an outer portion both of the portions being movable to vary the inductance of the inductor.

22. A prosthesis as claimed in claim 1 incorporating a member movable by an electric motor, wherein operation of the electric motor is controlled by a control circuit which, in a first state thereof, conditions the drive motor to drive the movable member in one sense; which, in a second state thereof, conditions the motor to drive the movable member in the opposite sense; and which, in a third state thereof, conditions the motor to act as a brake to retard motion of the movable member.

23. A prosthesis as claimed in claim 22, wherein the electric motor is a direct current motor and is operable as a brake by the provision of a high conductivity shunt across it.

* * * * *